United States Patent
Shih et al.

(10) Patent No.: US 9,060,989 B2
(45) Date of Patent: Jun. 23, 2015

(54) METHOD FOR TREATING OR RELIEVING INFLAMMATORY BOWEL DISEASE

(71) Applicant: INDUSTRIAL TECHNOLOGY RESEARCH INSTITUTE, Hsinchu County (TW)

(72) Inventors: Ying-Chu Shih, Zhubei (TW); Lain-Tze Lee, Hsinchu (TW); Nai-Yun Hu, Douliu (TW); Tien-Soung Tong, Taichung (TW)

(73) Assignee: INDUSTRIAL TECHNOLOGY RESEARCH INSTITUTE, Hsinchu County (TW)

( * ) Notice: Subject to any disclaimer, the term of this patent is extended or adjusted under 35 U.S.C. 154(b) by 220 days.

(21) Appl. No.: 13/631,620

(22) Filed: Sep. 28, 2012

(65) Prior Publication Data

US 2013/0022694 A1     Jan. 24, 2013

Related U.S. Application Data

(62) Division of application No. 13/118,413, filed on May 28, 2011, now abandoned.

(60) Provisional application No. 61/360,190, filed on Jun. 30, 2010.

(30) Foreign Application Priority Data

Dec. 15, 2010   (TW) .............................. 99143928 A

(51) Int. Cl.
    A61K 36/00       (2006.01)
    A61K 36/233      (2006.01)
(52) U.S. Cl.
    CPC .................................... A61K 36/233 (2013.01)
(58) Field of Classification Search
    None
    See application file for complete search history.

(56) References Cited

FOREIGN PATENT DOCUMENTS

| CN | 1132093 | A | * | 10/1996 |
| CN | 1240147 | A |   | 1/2000 |
| CN | 1275396 | A | * | 12/2000 |
| CN | 1899333 | A |   | 1/2007 |
| CN | 101288744 | A |   | 10/2008 |
| CN | 102106884 | A |   | 6/2011 |
| EP | 0968718 | A1 |   | 1/2000 |
| JP | 06227997 | A | * | 8/1994 |

OTHER PUBLICATIONS

Yang et al, Identification and determination of the saikosaponins in Radix bupleuri by accelerated solvent extraction combined with rapid-resolution LC-MS. Journal of Separation Science, (Jul. 2010) vol. 33, No. 13, pp. 1933-1945.*
Endo et al, Suppression of murine colitis by Kampo medicines, with special reference to the efficacy of saireito. Journal of Traditional Medicines (2009), vol. 26, No. 3, pp. 110-121.*
Extended European Search Report, issued Oct. 17, 2011, for counterpart application filed with EPO (11171756.7-2107).
Bremner, "Phenylpropanoid NF-[kappa]B inhibitors from *Bupleurum fruticosum*", Planta Medica, vol. 70, pp. 914-918 (Oct. 2004).
Notification of first examination opinion issued by the China Intellectual Property Office on Sep. 6, 2012, for the above-referenced application's counterpart application in China (Application No. 201010612036.7).
Wong et al., "Mechanistic Study of Saikosaponin-d (Ssd) on Suppression of Murine T Lymphocyte Activation", Journal of Cellular Biochemistry, 107:303-315 (2009).
Li et al., "Pathogenesis and treatment of Crohn's disease", Infeet Dis Info, 2009, vol. 22, No. 3.
Dong et al., "Application and development of anti-tumor necrosis factor therapies in Crohn disease", 2006, vol. 26, No. 2.
Office Action (Notification of Examination Opinion) issued by the Taiwan Intellectual Property Office on Jan. 18, 2013, for the above-referenced application's counterpart application in Taiwan (Application No. 099143928).
Weng, "The Effect of *Bupleurum kaoi* Against Dimethylnitrosamine-Induced Hepatic Fibrosis in Rat", Kaohsiung Medical University, Master's Thesis, Jun. 2004.
Office Action (Notification of Second Examination Opinion) issued by China's State Intellectual Property Office on May 3, 2013, for the above-referenced application's counterpart application in China (Application No. 201010612036.7).
Sun Y.et al.,"Saikosaponin a inhibits the proliferation and activation of T-cells through cell cycle arrest and induction of apoptosis", International Immunopharmacology 9 (2009) 978-983.

* cited by examiner

*Primary Examiner* — Qiuwen Mi
(74) *Attorney, Agent, or Firm* — Pai Patent & Trademark Law Firm; Chao-Chang David Pai

(57) ABSTRACT

A method for treating or relieving inflammatory bowel disease (IBD) is provided, including administering an extract of *Bupleurum* as an active ingredient to a subject. The *Bupleurum* may be selected from the group consisting of *Bupleurum krylovianum, Bupleurum chinense, Bupleurum commelynoideum, Bupleurum scorzonerifolium, Bupleurum triradiatum, Bupleurum falcatum, Bupleurum kaoi* and a combination thereof.

8 Claims, 10 Drawing Sheets

METHOD FOR TREATING OR RELIEVING INFLAMMATORY BOWEL DISEASE

CROSS REFERENCE TO RELATED APPLICATIONS

This application claims the benefit of U.S. patent application Ser. No. 13/118,413, filed May 28, 2011, which claims the benefit of U.S. Provisional Application No. 61/360,190, filed Jun. 30, 2010 and claims the priority of Taiwan Patent Application No. 099143928, filed Dec. 15, 2010, the entire contents of which are hereby incorporated by reference.

BACKGROUND

1. Technical Field

The disclosure relates to an extract of Bupleurum as an active ingredient for treating or relieving inflammatory bowel disease (IBD).

2. Description of the Related Art

The current medicament for inflammatory bowel disease (IBD) is commonly categorized into four groups, (1) immunosuppression drugs, such as azathioprine, cyclosporine or steroids, (2) therapeutic agents, such as sulfsalazine or 5-aminosalicylic acid (5-ASA), (3) biological agents for inhibiting specific inflammatory factors, such as infliximab or remicade, and (4) anti-diarrheal agents. However, these medicaments may not completely cure IBD and sometimes cause side effects.

A new generation of drugs for rheumatoid arthritis by inhibiting the tumor necrosis factor (TNF-α) has also been used for the treatment of IBD, such as etanercept, adalimumab, or the like. These drugs show good drug effects during a short period of time and immune tolerance, but due to its price, intravenous injection, a potential immunoresponse and limited test data, clinical use has been limited.

*Bupleurum* is a medicinal plant recorded in a Chinese herbal medicine book, Shennong bencao jiing. It is traditionally used for relieving fever, pain and inflammatory diseases and treating irritations, infections causing fever, thirst, jaundice and hepatitis, etc. The *Bupleurum* root is known for its medicinal effect and has been chemically isolated. Saikosaponin, longispinogenin, steroids, fatty oils, flavonoids and saccharides have been isolated from the extract of the *Bupleurum* root, in which saikosaponin is the primary component.

It is known that attempts have been made in biological medicine, to use *Bupleurum* in treating hepatitis. Nevertheless, no study or reference for using *Bupleurum* to treat IBD has been found. Accordingly, a specific extraction method of *Bupleurum* was used to develop a novel pharmaceutical composition and method for treating or relieving IBD, wherein the correlations between a *Bupleurum* extract and IBD were identified.

SUMMARY

In one embodiment of the disclosure, a pharmaceutical composition for treating or relieving inflammatory bowel disease is provided, which comprises an extract of *Bupleurum* as an active ingredient.

In another embodiment of the disclosure, a method for treating or relieving inflammatory bowel disease is provided, which comprises administering an extract of *Bupleurum* as an active ingredient to a subject.

In a further embodiment of the disclosure, a method for preparing a medicament of treating or relieving inflammatory bowel disease is provided, which comprises a step of providing an extract of *Bupleurum* as an active ingredient in preparation of a medicament of treating or relieving inflammatory bowel disease.

DETAILED DESCRIPTION

Figure 1:
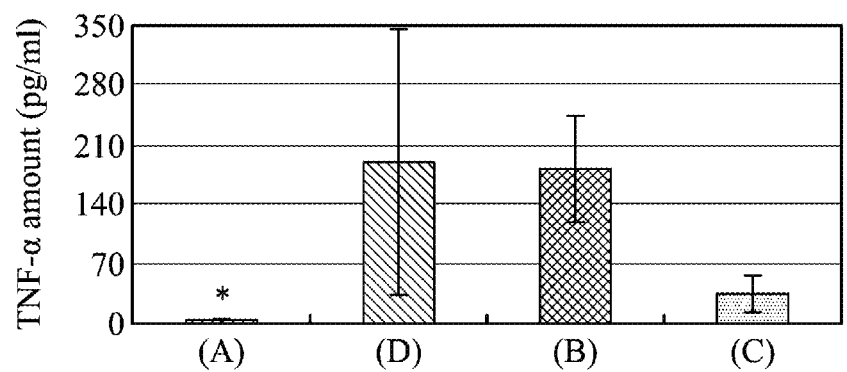
FIG. 1 is the amount of TNF-α in a bowel infusion, in which column (A) refers to a negative control, column (B) refers to a vehicle treatment with an enteritis induction of TNBS and no administration of a *Bupleurum* extract, column (C) refers to one embodiment of the invention with oral administration of 100 mg/kg of a *Bupleurum krylovianum* extract by the enteritis animal model, and column (D) refers to a positive control with oral administration of 200 mg/kg of 5-ASA by the enteritis animal model.
Figure 2:
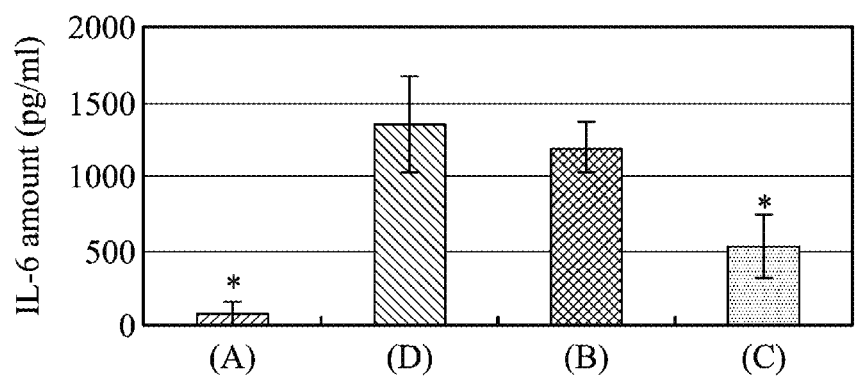
FIG. 2 is the amount of IL-6 in a bowel infusion, in which the representation of the columns are identical to those in FIG. 1.
Figure 3:
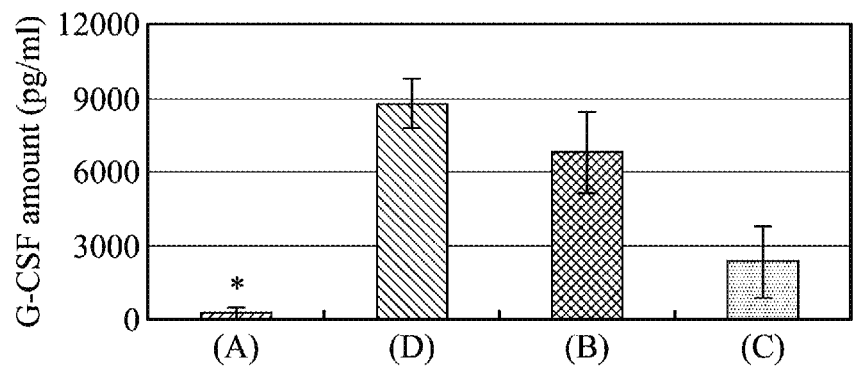
FIG. 3 is the amount of G-CSF in a bowel infusion, in which the representation of the columns are identical to those in FIG. 1.
Figure 4:
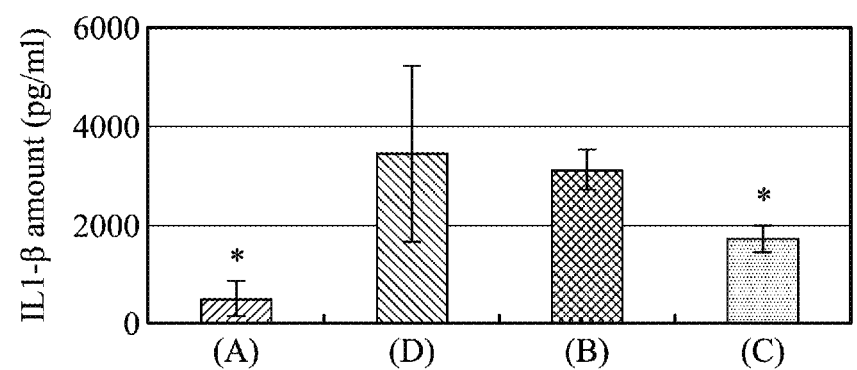
FIG. 4 is the amount of IL1-β in a bowel infusion, in which the representation of the columns are identical to those in FIG. 1.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The *Bupleurum* species in the disclosure are selected from the family which is slightly cold in nature and bitter to the taste according to page-78 in "The English-Chinese Encyclopedia of Practical Traditional Chinese medicine vol.2: The Chinese Materia Medica"(Higher Education Press, Beijing, China, 1994 edition 1.)

More specific, the *Bupleurum* species in the application are selected from the group consisting of *Bupleurum krylovianum, Bupleurum chinense, Bupleurum commelynoideum, Bupleurum scorzonerifolium, Bupleurum triradiatum, Bupleurum falcatum, Bupleurum kaoi* and a combination thereof.

The *Bupleurum* can be extracted from the root of a plant or a whole plant as described in U.S. patent application Ser. No. 12/829,357 (Jul. 1, 2010) which is incorporated by reference. The "extraction" according to the disclosure can be solvent extraction. The "solvent extraction" is directed to a method comprising: adding a substrate of interest into a suitable solvent and extracting a target compound based on the solubility of components of the substrate in the solvent. In one example, the *Bupleurum* is ground and immerged in a solvent under room temperature for a period of time. The solvent is isolated and dried under room temperature to obtain an extract of the *Bupleurum*. In another example, the ground *Bupleurum* is added into a polar solvent and extracted after heating under reflux.

The solvent used in the invention can be $C_1$~$C_{12}$ alcohols, $C_2$~$C_5$ acetates, $C_5$~$C_6$ alkanes, or combinations thereof, such as methanol, ethanol, propanol, isopropanol, butanol, 2-butyl alcohol, tert-butyl alcohol, 1,3-butandiol, 1,4butandiol, pentanol, isopentanol, 2,3-pentandiol, 2,4-pentandiol, cyclopentanol, hexanol, cyclohexanol, heptanol, octanol, nonanol, decanol, undecanol, dodecanol, ethyl acetate, propyl acetate, pentyl acetate, pentane, cyclopentane, hexane, cyclohexane, or combinations thereof, but are not limited thereto. In one example, ethanol, ethyl acetate and/or pentane is/are used as a solvent for extraction. In another example, an ethanol aqueous solution is used as a solvent for extraction. The concentration of ethanol can be about 20%~95%, or about 40%~95% based on the ethanol aqueous solution.

The volume of the solvent can be more than 5 times that of the *Bupleurum*, or about 5~10 times.

The extraction may last more than two hours. In one embodiment, the extraction lasts for about 2~24 hours or about for 4~5 hours.

The extraction is usually performed at room temperature. In one embodiment, the extraction is performed at a temperature from room temperature to the temperature of the ethanol aqueous solution is boiled and refluxed.

The extraction may further comprise a step of concentration by drying, wherein a solid or crystal form is extracted after being heated and refluxed. The extraction process can be repeated several times for a pure extract.

The animal model of enteritis for test is from an induction by trinitrobenzene sulfonic acid (TNBS) (Current Protocols in Immunology (2001) 15.19.1-15.19.14; Lahat G, Halperin D, Fabian I, et al. Immunomodulatory Effects of Ciprofloxacin in TNBS-Induced Colitis in Mice. Inflamm Bowel Dis 2007;13:557-565; ten Hove T, van den Blink B, Pronk I, et al. Dichotomal role of inhibition of p38 MAPK with SB 203580 in experimental colitis. Gut 2002; 50:507-512; and Bouma G, Strober W. The Immunological and Genetic Basis of Inflammatory Bowel Disease. Nature Review Immunology 2003; 3: 521-533). The bowel in the animal model of enteritis has swelled and the feces therein show a mushy or watery appearance instead of a normal semi-solid type appearance. In one embodiment, the size of the swelled bowel is obviously reduced and the feces become soft blobs after an administration of the *Bupleurum* extract. The result reveals that the extract of *Bupleurum* has effects on inhibition and alleviation of IBD. In one embodiment, the level of TNF-α, IL-6, G-CSF and IL1-β in a bowel infusion of the IBD is significantly decreased, suggesting that these factors correlate to the IBD.

According to the disclosure, the extract of *Bupleurum* is useful to ameliorate or cure IBD in a subject, including Crohn's disease, or enteritis or a bowel disease with an inflammatory symptom.

The subject described herein comprises a mammal, such as mouse, dog, cat, horse, goat, pig, monkey, chimpanzee, and particularly, human.

The subject is administered the extract of *Bupleurum* in an effective amount. The effective amount is not specifically limited, and can be adjusted by a person skilled in the art based on a subject's age, physical condition or inflammatory levels. The effective amount for administration is about 50~1,000 mg/kg or about 30~500 mg/kg based on the weight of the subject.

The pharmaceutical composition according to the invention may further comprise a pharmaceutically acceptable carrier and/or additive added in an appropriate ratio based on the dosage form, storage type or administration route.

The administration route in the invention comprises intravenous, intramuscular, subcutaneous or oral routes. Oral administration is preferable. The pharmaceutical composition of the invention can be administered in a multiple dose regime within a period of time. The administrative regime can be estimated and identified according to routine pharmaceutical practices.

EXAMPLE 1

Extraction of *Bupleurum*

The extraction of the *Bupleurum* species is based on U.S. patent application Ser. No. 12/829,357 (Jul. 1, 2010) with modification. Specifically, the roots of *Bupleurum krylovianum, Bupleurum chinense, Bupleurum commelynoideum, Bupleurum scorzonerifolium, Bupleurum triradiatum, Bupleurum falcatum* and *Bupleurum kaoi* were separately grinded into powdered form.

0.5 g of each the powdered form were added to 25 ml of an ethanol aqueous solution in a concentration of 25%, 50%, 75% and 95% by volume, respectively. Each of the solution was vibrated at room temperature overnight. After being dried and concentrated, extracts of *Bupleurum* were obtained, respectively.

EXAMPLE 2

Inhibition of TNF-α, IL-6, G-CSF and IL1β in a Bowel Infusion

The examples discussing inhibition of TNF-α, IL-6, G-CSF and IL1-β in a bowel infusion by the extract of

*Bupleurum*, are based on the references in the following with some modifications: Current Protocols in Immunology (2001) 15.19.1-15.19.14; Lahat G, Halperin D, Fabian I, et al. Immunomodulatory Effects of Ciprofloxacin in TNBS-Induced Colitis in Mice. Inflamm Bowel Dis 2007;13:557-565; ten Hove T, van den Blink B, Pronk I, et al. Dichotomal role of inhibition of p38 MAPK with SB 203580 in experimental colitis. Gut 2002;50:507-512; and Bouma G, Strober W. The Immunological and Genetic Basis of Inflammatory Bowel Disease. Nature Review Immunology 2003; 3: 521-533.

Specifically, BABL/cAnNCrlBltw mice, purchased from BioLASCO Taiwan (Bltw) were grouped into four groups having 6 mice to a group. In three of the groups, each mouse was injected with 1.75 mg of trinitrobenzene sulfonic acid (TNBS) (Sigma) at a 4 cm depth of the bowel from the anus. After 48 hours, the injected location was induced to form enteritis. Mice in another group were injected with a 50% ethanol aqueous solution without TNBS at a 4 cm depth of the bowel from the anus as a negative control (A). The location injected ethanol aqueous solution without TNBS was not induced to form enteritis. The test article or vehicle control was administered at 4 hours and 24 hours after the TNBS induction, and the animal were sacrificed after 48 hours of TNBS induction.

In one of the enteritis-induced groups, a 6 cm length cut was made from the anus of the mice of the enteritis-induced bowel as a vehicle treatment (B). The cut bowel was immerged in phosphate buffer saline (PBS) for 2 hours.

In one of the enteritis-induced group, the mice were fed 100 mg/kg of *Bupleurum krylovianum* extract, extracted by the extraction of the 50% ethanol aqueous solution in Example 1. Then, a 6 cm length cut was made from the anus of the mice of the enteritis-induced bowel as a test group (C). The cut bowel was immerged in phosphate buffer saline (PBS) for 2 hours.

In another one of the enteritis-induced group, the mice were fed 200 mg/kg of 5-aminosalicyclic acid (5-ASA). Then, a 6 cm length cut was made from the anus of the mice of the enteritis-induced bowel as a positive control (D). The cut bowel was immerged in phosphate buffer saline (PBS) for 2 hours.

The bowel infusion of the groups (A), (B), (C) and (D) were respectively quantified and analyzed, for the amounts of TNF-α, IL-6, G-CSF and IL1-β by an ELISA (R&D Systems®). The results are shown in FIGS. 1~4, respectively.

EXAMPLE 3

Improvement of Bowel Swelling and Mushy or Watery Feces

BABL/c Mice were induced to form enteritis as in the steps of Example 2. The enteritis-induced mice were separated into groups and each were fed with 100 mg/kg of *Bupleurum krylovianum* (100 mg/kg DLS01=080221-001, extracted with 50% EtOH aqueous solution), 1000 mg/kg of *Bupleurum krylovianum* (extracted with 50% EtOH aqueous solution), 100 mg/kg of *Bupleurum chinense* (DLS01-12 100 mg/kg, extracted with 50% EtOH aqueous solution), 100 mg/kg of *Bupleurum commelynoideum* (DLS01-41 100 mg/kg, extracted with 50% EtOH aqueous solution), 100 mg/kg of *Bupleurum scorzonerifolium* (DLS01-53 100 mg/kg, extracted with 50% EtOH aqueous solution), 100 mg/kg of *Bupleurum triradiatum* (DLS01-69 100 mg/kg, extracted with 50% EtOH aqueous solution), 100 mg/kg of *Bupleurum falcatum* (BEL-0506 100 mg/lg, extracted with 50% EtOH aqueous solution), and 100 mg/kg of *Bupleurum kaoi* (BEL-1153 100 mg/lg, extracted with 50% EtOH aqueous solution). Then, a 6 cm length cut was made from the anus of the mice of the enteritis-induced bowel to observe the swelling and the type of feces thereof (FIGS. 7~14).

Figure 5:
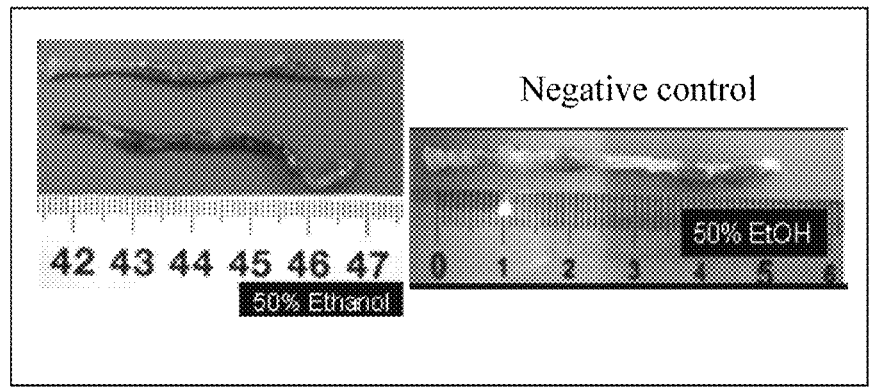
FIG. 5 is the type of the bowel in the negative control with an injection of a 50% ethanol aqueous solution without TNBS, in which the diameter of the bowel is about 1 mm and the appearance of the feces is semi-solid.
Figure 6:
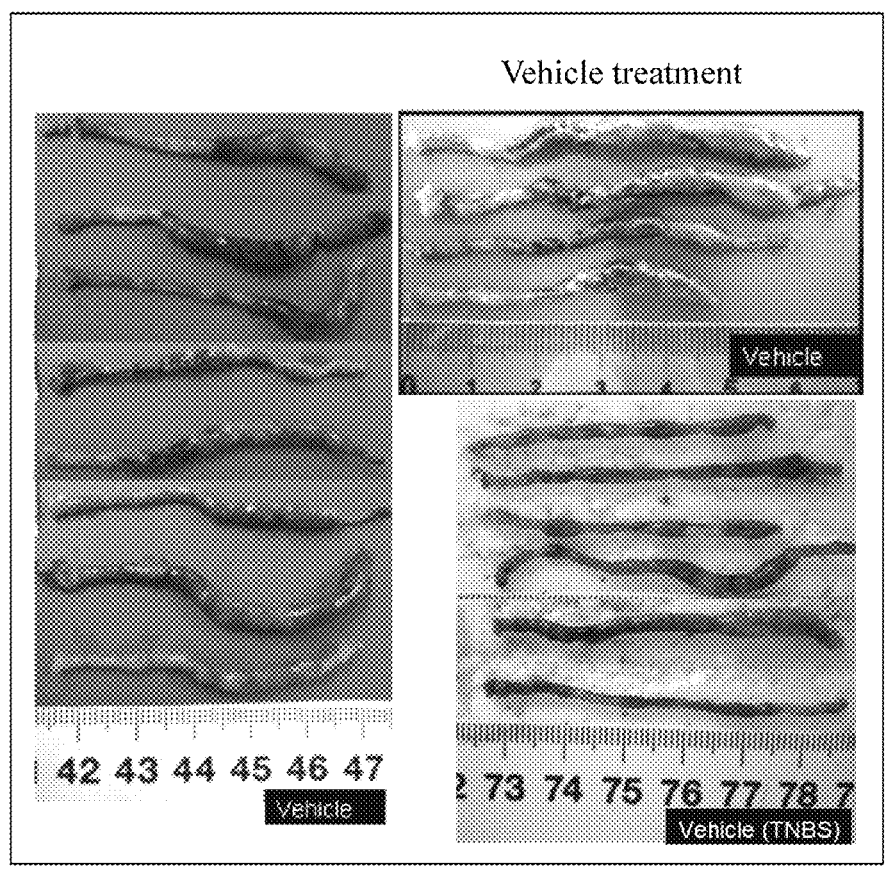
FIG. 6 is the type of the bowel in the vehicle treatment with an enteritis induction of TNBS and no administration of a *Bupleurum* extract, in which the diameter of the bowel is about 35 mm and the appearance of the feces is mushy and watery.
Figure 7:
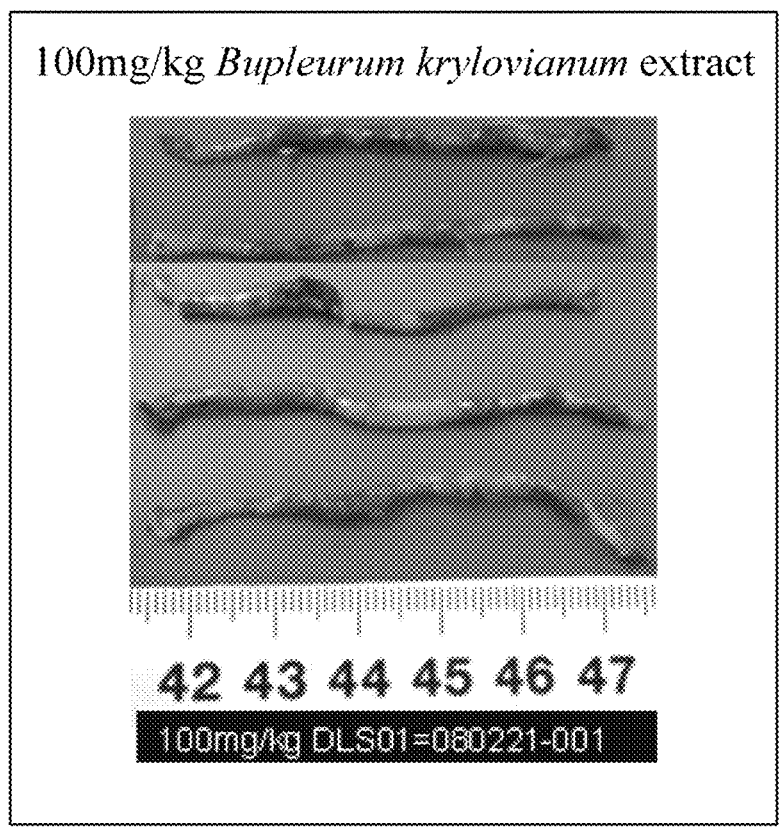
FIG. 7 is the type of the bowel in one embodiment of the invention with an enteritis induction of TNBS and oral administration of 100 mg/kg of a *Bupleurum krylovianum* extract (100 mg/kg DLS01=080221-001)
Figure 8:
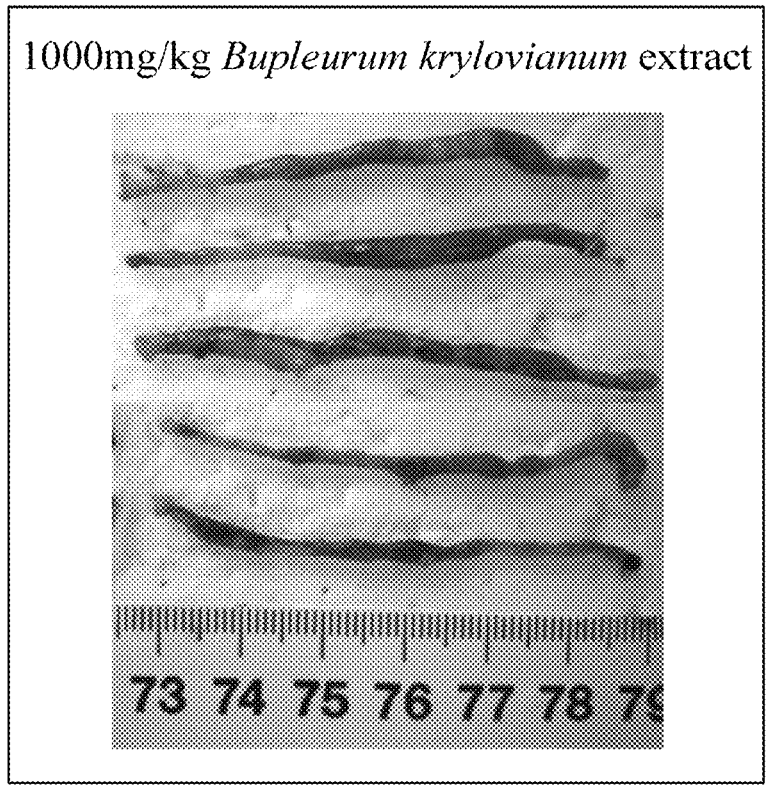
FIG. 8 is the type of the bowel in one embodiment of the invention with an enteritis induction of TNBS and oral administration of 1000 mg/kg of a *Bupleurum krylovianum* extract (1000 mg/kg DLS01=080221-001)
Figure 9:
FIG. 9 is the type of the bowel in one embodiment of the invention with an enteritis induction of TNBS and oral administration of 100 mg/kg of a *Bupleurum chinense* extract (DLS01-12 100 mg/kg)
Figure 10:
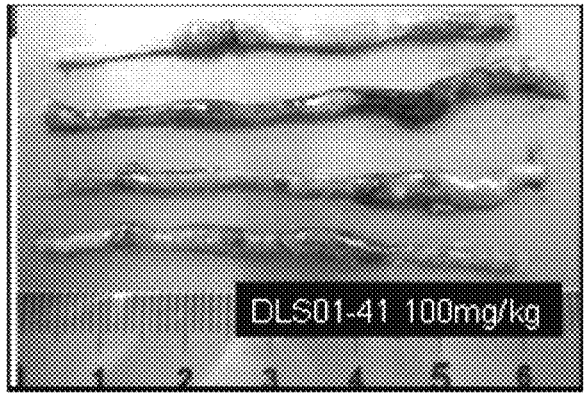
FIG. 10 is the type of the bowel in one embodiment of the invention with an enteritis induction of TNBS and oral administration of 100 mg/kg of a *Bupleurum commelynoideum* extract (DLS01-41 100 mg/kg)
Figure 11:
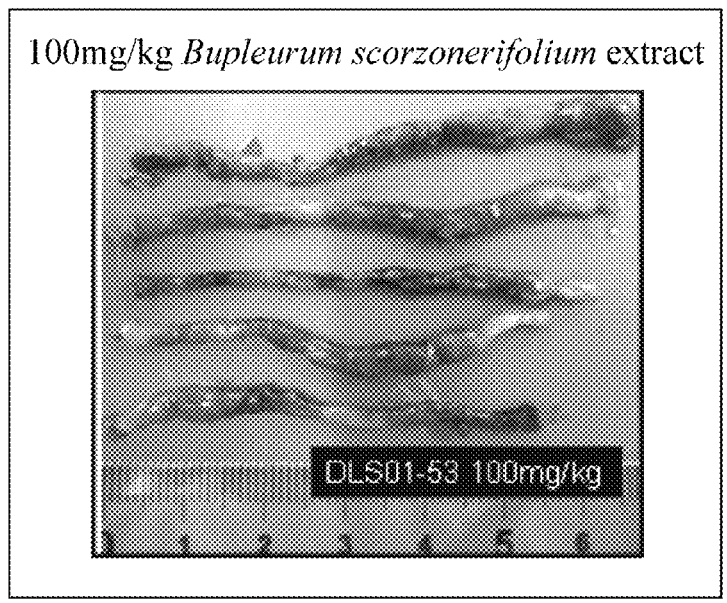
FIG. 11 is the type of the bowel in one embodiment of the invention with an enteritis induction of TNBS and oral administration of 100 mg/kg of a *Bupleurum scorzonerifolium* extract (DLS01-53 100 mg/kg)
Figure 12:
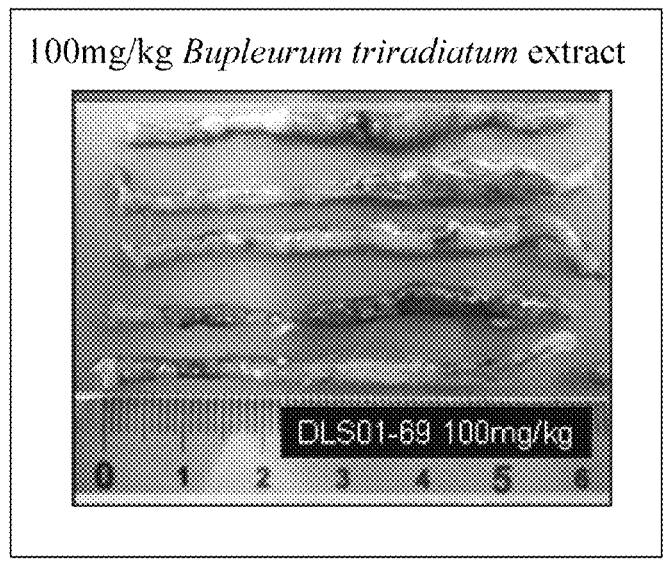
FIG. 12 is the type of the bowel in one embodiment of the invention with an enteritis induction of TNBS and oral administration of 100 mg/kg of a *Bupleurum triradiatum* extract (DLS01-69 100 mg/kg)
Figure 13:
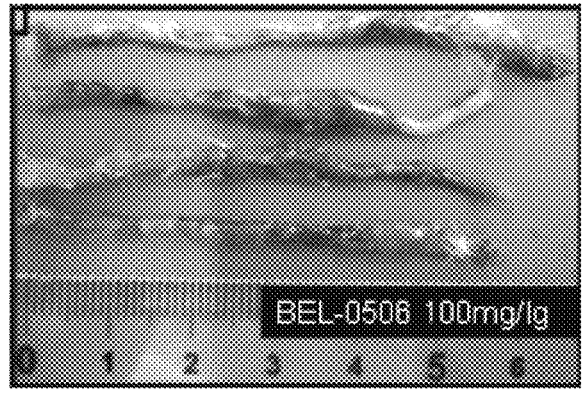
FIG. 13 is the type of the bowel in one embodiment of the invention with an enteritis induction of TNBS and oral administration of 100 mg/kg of a *Bupleurum falcatum* extract (BEL-0506 100 mg/lg)
Figure 14:
FIG. 14 is the type of the bowel in one embodiment of the invention with an enteritis induction of TNBS and oral administration of 100 mg/kg of a *Bupleurum kaoi* extract (BEL-1153 100 mg/lg)
Figure 15:
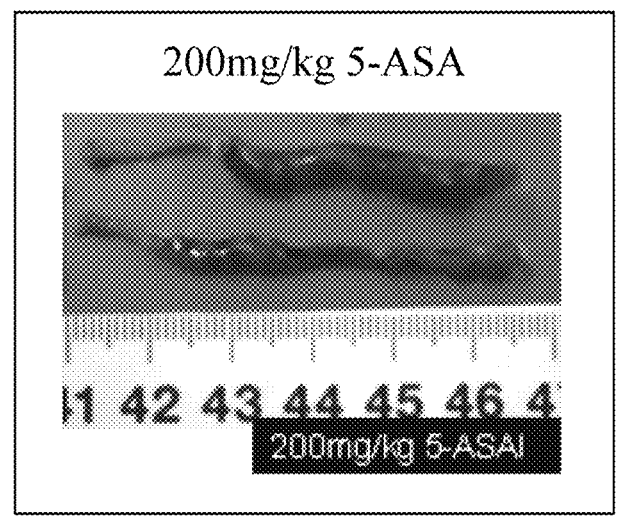
FIG. 15 is the type of the bowel in the positive control with an enteritis induction of TNBS and oral administration of 200 mg/kg of 5-ASA (200 mg/kg 5-ASA1).

The bowels from the negative control (A), vehicle treatment (B) and positive control (D) (200 mg/kg 5-ASA) in Example 2 were also observed and the swelling and the type of feces were recorded, as shown in FIGS. 5,6 and 15, respectively.

The enteritis model in the vehicle treatment without the administration of the *Bupleurum* extract showed bowel swelling and mushy and watery feces (FIG. 6). However, in the enteritis model with the administration of the *Bupleurum* extract, the bowel swelling was reduced and soft blobs and semi-solid feces were formed (FIGS. 7~14). The result showed an improvement of enteritis. Meanwhile, the bowel swelling was not alleviated or eliminated in the positive control (5-ASA); noting that 5-ASA is currently used as the therapeutic drug for treating IBD.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method for treating or relieving inflammatory bowel disease, comprising administering an ethanol extract of *Bupleurum* as a sole active ingredient to a subject suffering from inflammatory bowel disease, wherein the *Bupleurum* is extracted with an ethanol aqueous solution in a concentration of 20~95% by volume, and the extract of *Bupleurum* is administered in an amount of 50~1000 mq/kq based on the subject's weight.

2. The method as claimed in claim 1, wherein the *Bupleurum* is selected from a species which is slightly cold in nature and bitter to the taste.

3. The method as claimed in claim 1, wherein the *Bupleurum* is selected from the group consisting of *Bupleurum krylovianum, Bupleurum chinense, Bupleurum commelynoideum, Bupleurum scorzonerifolium, Bupleurum triradiatum, Bupleurum falcatum, Bupleurum kaoi* and a combination thereof.

4. The method as claimed in claim 1, wherein the extract of *Bupleurum* is extracted from the root thereof.

5. The method as claimed in claim 1, wherein the ethanol aqueous solution is in a concentration of about 40~95% by volume.

6. The method as claimed in claim 1, wherein the inflammatory bowel disease comprises Crohn's disease, enteritis or a bowel disease with an inflammatory symptom.

7. The method as claimed in claim 1, wherein the extract of *Bupleurum* is orally administered.

8. The method as claimed in claim 1, wherein the subject comprises a human.

* * * * *